United States Patent [19]

Rueppel

[11] 4,035,176

[45] July 12, 1977

[54] N-(PERFLUOROACYL)-N-PHOSPHONOMETHYL GLYCINE COMPOUNDS, METHOD OF PREPARING SAME

[75] Inventor: Melvin L. Rueppel, Kirkwood, Mo.

[73] Assignee: Monsanto Company, St. Louis, Mo.

[21] Appl. No.: 682,244

[22] Filed: May 3, 1976

Related U.S. Application Data

[63] Continuation-in-part of Ser. No. 580,252, May 23, 1975, Pat. No. 3,970,695.

[51] Int. Cl.² .................... A01N 9/36; C07F 9/02
[52] U.S. Cl. ..................... 71/86; 260/502.5; 260/534 R; 260/545 R; 260/935
[58] Field of Search ............ 260/502.5, 534 R, 935; 71/86

[56] References Cited

U.S. PATENT DOCUMENTS

| | | | |
|---|---|---|---|
| 3,456,039 | 7/1969 | Beriger | 71/86 |
| 3,853,530 | 12/1974 | Franz | 260/502.5 |

*Primary Examiner*—James O. Thomas, Jr.
*Assistant Examiner*—G. T. Breitenstein
*Attorney, Agent, or Firm*—William T. Black; Donald W. Peterson

[57] ABSTRACT

N-(perfluoroacyl)-N-phosphonomethyl glycine compounds are prepared by the reaction of N-phosphonomethyl glycine with perfluoroacyl anhydrides employing an excess of the perfluoroalkanoic acid as the solvent. The N-(perfluoroacyl)-N-phosphonomethyl glycine compounds are useful as post-emergent herbicides and as sugar cane ripeners.

12 Claims, No Drawings

N-(PERFLUOROACYL)-N-PHOSPHONOMETHYL GLYCINE COMPOUNDS, METHOD OF PREPARING SAME

This application is a continuation-in-part of application Ser. No. 580,252, filed May 23, 1975 now U.S. Pat. No. 3,970,695.

This invention relates to a process for producing N-(perfluoroacyl)-N-phosphonomethyl glycine compounds, to the compounds produced and to the herbicidal use thereof. More particularly, this invention relates to the preparation of N-(perfluoroacyl)-N-phosphonomethyl glycine compounds by the reaction of a perfluoroacyl anhydride with N-phosphonomethyl glycine in a solvent consisting of a perfluoroalkanoic acid. This invention also relates to the post-emergent herbicidal use of the N-perfluoroacyl-N-phosphonomethyl glycine compounds produced.

N-acyl-N-phosphonomethyl glycine compounds are known as well as their use as herbicides. These acyl compounds are relatively weak post-emergent herbicides. Their weak activity as herbicides is believed to be the result of the inactivating effect of the hydrolytically stable acyl groups replacing the nitrogen-bonded hydrogen of N-phosphonomethyl glycine. In fact, it has been shown that when the N-benzoyl-; N-formyl and N-acetyl derivatives of N-phosphonomethyl glycine are added to water there is no detectable hydrolysis whereas the perfluoroacyl derivatives are completely hydrolyzed within 24 hours.

In accordance with the process of this invention N-perfluoroacyl derivatives of N-phosphonomethyl glycine are produced by forming an admixture of N-phosphonomethyl glycine and a perfluoroalkanoic acid and then adding thereto a perfluoroacyl anhydride and maintaining the resulting admixture at a temperature sufficiently elevated so as to cause said N-phosphonomethyl glycine and said perfluoroacyl anhydride to react to produce the N-perfluoroacyl derivatives of N-phosphonomethyl glycine. These derivatives have the formula

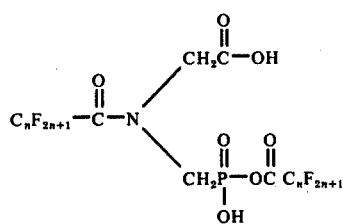

wherein $n$ is an integer of from 1 to 4.

The compounds of formula I can then be treated with water to hydrolyze the perfluoroacyl group attached to the —$PO_3$ group and replace that perfluoroacyl group with a hydrogen.

The novel compounds of this invention have the formula

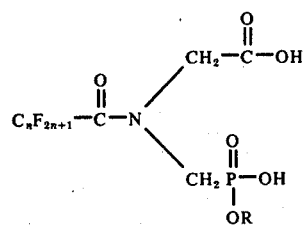

wherein R is a H or

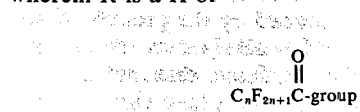

and $n$ is an integer of from 1 to 4.

The perfluoroalkanoic acids which are useful as the solvents for the process of the instant invention have the formula

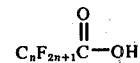

wherein $n$ is from 1 to 4 and includes trifluoroacetic acid, pentafluoropropionic acid, heptafluorobutyric acid and nonafluoropentanoic acid. Without the use of such solvents it has been found that the N-phosphonomethyl glycine is not sufficiently soluble in the anhydride so that the reaction will take place. It is therefore considered that the perfluoroalkanoic acid solvent is essential to the process of this invention.

The perfluoroanhydrides which are useful in the process of this invention are those having the formula

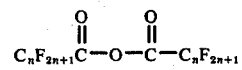

wherein each $n$ is an integer of from 1 to 4. For ease of reaction and ease of recovery of the reaction product, it is preferred that the $n$'s have the same value and further the $n$ of the perfluoroalkanoic acid also has the same value. The perfluoroalkanoic anhydrides useful in the process of this invention include trifluoroacetic anhydride, perfluorobutyric anhydride, perfluoropropionic anhydride and the like and mixed trifluoroacetic-heptafluorobutyric; pentafluoropropionic-heptafluorobutyric anhydrides and the like.

In conducting the process of this invention the temperature should be sufficiently elevated so as to initiate and sustain the reaction but not so elevated so as to cause undue decomposition of the reaction product or to produce side reactions. Generally reaction temperatures in the range of from about 20° C. to about 60° C. are preferred. It is even more preferred to conduct the reaction at temperatures of from 35° to 55° C.

The weight ratio of the reactants can vary over side ranges. It is of course apparent to those skilled in the art that one molecule of the anhydride reacts with one molecule of N-phosphonomethyl glycine to produce the product. It is therefore preferred to employ at least one mole of the anhydride for each mole of the N-phosphonomethyl glycine. It is even more preferred to employ from 0.5 to 3.0 moles of the anhydride for each mole of the N-phosphonomethyl glycine, for ease of reaction and ease of recovery of the reaction products.

The present process is generally conducted at atmospheric pressure. Although higher or lower pressure can be employed no commensurate advantages are obtained thereby.

The N-perfluoroacyl-N-phosphonomethyl glycines of this invention are useful as post-emergent herbicides and as sugar cane ripeners. The process of this invention is particularly useful in the analytical determination of and isolation of the metabolites of N-phosphonomethyl glycine which contain a reactive nitrogen. The compounds produced by the process of this invention can be converted to alkyl esters employing a diazoalkane such as diazomethane, diazobutane, etc. and the esters recovered by vapor phase chromatography. It has been found that this technique is useful where extremely small amounts of such derivatives are found.

In the following examples, which illustrate the invention, all parts and percents are by weight unless otherwise indicated.

EXAMPLE 1

16.9 g. of N-phosphonomethyl glycine (0.1 mole) was placed in a flask. 400 g. of trifluoroacetic acid (3.5 moles) was added in one portion followed immediately by the addition of 400 g. of trifluoroacetic acid anhydride (1.9 moles). The flask and its contents were stirred mechanically and warmed at 40°–45° C. for about 1 hour until a homogeneous solution was obtained. The unreacted trifluoroacetic acid and anhydride were removed in vacuo at 50° C. to give 36.0 g. of bis(N,O-trifluoroacetyl)-N-phosphonomethyl glycine having the formula

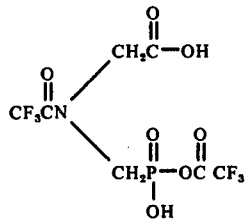

The amorphous solid was analytically pure having the following elemental composition: Cal'd. %C, 23.6; %H, 1.5; %N, 4.1; %O, 31.1; %P, 8.6. Found %C, 23.28; %H, 1.68; %N, 3.88; %O, 31.02; %F, 31.57; %P, 8.58. Analysis by nuclear magnetic resonance showed the product to be substantially pure bis (N,O-trifluoroacetyl)-N-phosphonomethyl glycine.

EXAMPLE 2

13.5 g. of N-phosphonomethyl glycine (0.08 moles) was placed in a flask. 400 g. of heptafluorobutyric acid (1.9 moles) was added in one portion followed immediately by the addition of 410 g. of heptafluorobutyric acid anhydride (1.0 mole) in one portion. The flask and its contents were stirred mechanically and warmed at 40°–45° C. for about 5 hours until a homogeneous solution was obtained. The unreacted heptafluorobutyric acid and anhydride were removed in vacuo at 40° C. to give 44.1 g. of bis (N,O-heptafluorobutyrl)-N-phosphonomethyl glycine having the formula

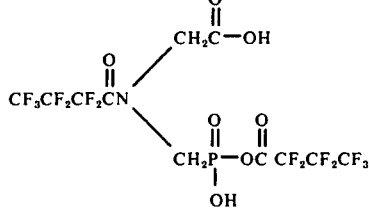

The amorphous solid was analytically pure having the following elemental composition: Calc'd. %C, 23.4; %H, 1.2; %N, 2.4; %O, 20.5; %F, 47.1; %P, 5.4. Found %C, 23.54; %H, 1.08; %N, 2.50; %O, 19.96; %F, 47.40; %P, 5.52.

Analysis by nuclear magnetic resonance showed the product to be substantially pure bis (N,O-heptafluorobutyryl)-N-phosphonomethyl glycine.

By following the procedure of Examples 1 and 2 but employing perfluoropropionic acid and perfluoropropionic acid anhydride one produces bis-(N,O-pentafluoropropanoyl)-N-phosphonomethyl glycine.

EXAMPLE 3

The post-emergence herbicidal activity of various compounds of this ivention is demonstrated as follows. The active ingredients are applied in spray form to 14 or 21 day old specimens of various plant species. The spray, a water or organic solvent-water solution containing active ingredient and a surfactant (35 parts butylamine salt of dodecylbenzene-sulfonic acid and 65 parts tall oil condensed with ethylene oxide in the ratio of 11 moles ethylene oxide to 1 mole tall oil), is applied to the plants in different sets of pans at several rates (kg per hectare) of active ingredient. The treated plants are placed in a greenhouse and the effects are observed and recorded after approximately 2 weeks or approximately 4 weeks, as is indicated in the last column of Table I.

The post-emergence herbicidal activity index used in Table I is as follows:

| PLANT RESPONSE | INDEX | PLANT RESPONSE | INDEX |
| --- | --- | --- | --- |
| No injury | 0 | Severe injury | 3 |
| Slight injury | 1 | Killed | 4 |
| Moderate injury | 2 | | |

The plant species utilized in these tests are identified by letter in accordance with the following legend:

A — Soybean
B — Sufar Beet
C — Wheat
D — Rice
E — Sorghum
F — Cocklebur
G — Wild Buckwheat
H — Morningglory
I — Hemp Sesbania
J — Lambsquarters
K — Smartweed
L — Velvetleaf
M — Downy Brome
N — Panicum Spp
O — Barnyardgrass
P — Crabgrass

TABLE I

| COMPOUND | RATE | A | B | C | D | E | F | G | H | I | J | K | L | M | N | O | P | WEEKS |
| --- | --- | --- | --- | --- | --- | --- | --- | --- | --- | --- | --- | --- | --- | --- | --- | --- | --- | --- |
| I | 0.224 | 1 | 0 | 0 | 0 | 0 | 1 | 0 | 0 | 0 | 0 | — | 0 | 0 | 0 | 0 | 0 | 2 |
| I | 1.12 | 1 | 1 | 1 | 0 | 0 | 0 | 0 | 1 | 0 | 1 | — | 1 | 1 | 0 | 1 | 1 | 2 |
| I | 1.12 | 0 | 2 | 1 | 0 | 1 | 1 | 1 | 1 | 0 | 2 | — | 1 | 2 | 2 | 2 | 3 | 4 |
| I | 4.48 | 1 | 3 | 3 | 0 | 1 | 1 | 2 | 1 | 2 | 2 | — | 2 | 1 | 4 | 2 | 3 | 4 |
| I | 4.48 | 1 | 4 | 3 | 1 | 3 | 2 | 2 | 2 | 1 | 3 | — | 3 | 3 | 4 | 3 | 4 | 2 |
| I | 11.2 | 2 | 3 | 3 | 3 | 3 | 3 | 1 | 2 | 2 | 3 | — | 3 | 3 | 4 | 4 | 4 | 4 |

TABLE I-continued

| COMPOUND | RATE | A | B | C | D | E | F | G | H | I | J | K | L | M | N | O | P | WEEKS |
|----------|------|---|---|---|---|---|---|---|---|---|---|---|---|---|---|---|---|-------|
| 1 | 11.2 | 3 | 4 | 4 | 4 | 3 | 3 | 2 | 3 | 2 | 4 | — | 4 | 4 | 4 | 4 | 4 | 2 |

Compound 1 is bis-(N,O-trifluoroacetyl) N-phosphonomethyl glycine.

EXAMPLE 4

This example gives the procedure and results obtained by applying a compound of this invention to sugar cane.

In determining the appropriate rates and times to apply the compounds of this invention to sugar cane plants, it is necessary to consider both the chronological age of the plant and its stage of maturity since cane, depending upon the practice in different geographical areas, is grown from 9 to about 30 months before harvest. Application at a rate of from about 0.1 to 5.0 pounds per acre can be made from about 2 to 8 weeks prior to the projected harvest date. Preferably, such applications are made from 3 to 7 weeks before said date.

An active ingredient of this invention can be conveniently applied to the plants as an aqueous solution or suspension. Said active ingredient can, of course, be in its free acid form, or it may be employed in the form of an alkali metal or amine salt in order to improve such desirable features as solubility or stability. For example, a liquid composition may be applied from a boom-spray, or a solid dust composition where the active component is diluted with an inert solid such as clay can be flown on the plants from an aircraft. Suitable liquid compositions include surfactants such as those enumerated in U.S. Pat. Nos. 3,224,865 and 3,245,775. Preferred surface active agents which are convenient to use in liquid compositions of this invention are of the non-ionic type such as alkyl phenoxy poly(ethyleneoxy)ethanols, polyethylene oxide adducts of fatty and resin acids, and long chain alkyl mercaptan adducts with ethylene oxide.

A particularly preferred carrier for the acids or salts of this invention is water with about 0.1 to 2.0% by weight of surfactant added thereto. Alternatively, the aqueous carrier can be replaced by a non-toxic mineral oil as such, or as an oil-in-water or water-in-oil emulsion. It has been found convenient to apply the compositions to the plants in the form of aqueous solutions, suspensions or emulsions, and dilution being such that a spray volume of from about 7 to 20 gallons of liquid per acre will contain the desired dosage of active ingredient. It will be recognized, however, that higher or lower total spray volumes can be beneficially employed depending upon the particular dispensing apparatus and other factors well understood by those skilled in the art.

The specific tests which follow are presented as illustrative, non-limiting demonstrations of the useful and unexpected properties of a number of representative compounds of this invention.

TEST PROCEDURE 0.5 Gram of a compound of the invention is dissolved in 4 ml. water that contains as a surfactant about 0.25% (w./w.) nonylphenol which was ethoxylated to contain about 10.5 mols. of ethylene oxide per mol. of nonylphenyl ("Tergitol NPX"). 0.6 ml. of this solution is deposited or dropped by means of a syringe with a fine needle on the spindle area at the top of the last visible dewlap of each of 20 stalks of sugar cane. (A dewlap is the junction between the blade of the leaf and the sheath which clasps the stalk). Ten of these stalks were harvested 4 weeks after such treatment and 10 more were harvested 5 weeks after such treatment.

The top 15 joints of the treated cane as well as those of similar untreated cane are removed, combined and analyzed in terms of juice purity and pol percent cane, following the so-called "press-method" developed by T. Tanimoto, Hawaiian Planters Record, 57, 133 (1964). "Pol percent cane" is a polarmetric determination and equals the percentage of sucrose if the latter is the only substance in the solution which will rotate the plant of polarized light. In any event, determination of the pol percent cane is a standard and effective method for determining the sucrose content of sugar cane. The results of two separate tests A and B are given below for the treated cane and for the untreated control in each test. The compound employed is indicated by the example number which describes its preparation.

|  | Treatment | Four Weeks | | Five Weeks | |
|---|---|---|---|---|---|
|  |  | Juice Purity | Pol % Cane | Juice Purity | Pol % Cane |
| Test A | Example 1 | 75.39 | 9.52 | 75.19 | 9.24 |
|  | Control | 69.06 | 7.32 | 64.22 | 6.53 |
| Test B | Example 1 | 77.62 | 9.32 | 84.79 | 12.60 |
|  | Control | 75.36 | 8.28 | 75.73 | 8.64 |

In applying the compositions of this invention to the plants which it is desired to control, it has been found to be desirable that the plant be emerged from the ground and even more desirable, that the plant be at least at the two leaf stage for maximum effect. It has been found that when the plants to be controlled have a portion of their growth above the ground or water, and the above-ground or above-water portion of the plant contacted with the herbicidal compositions of this invention at appropriate rates, the herbicide is translocated to kill such plant parts which are below the ground or water surface.

The phytotoxic compositions, including concentrates which require dilution prior to application to the plants, of this invention contain at least one active ingredient of this invention, that is, an N-perfluoroacyl-N-phosphonomethyl glycine, and an adjuvant in liquid or solid form. The compositions are prepared by admixing the active ingredient with an adjuvant including diluents, extenders, carriers and conditioning agents to provide compositions in the form of finely-divided particulate solids, solutions, dispersions or emulsions. Thus the active ingredient can be used with an adjuvant such as a finely-divided solid, a liquid of organic origin, water, a wetting agent, a dispersing agent, an emulsifying agent or any suitable combination of these. From the viewpoint of economy and convenience, water is the preferred diluent, particularly with the highly water-soluble glycine salts such as the alkali metal salts and amine and ammonium salts. With these derivatives, solutions containing as high as 0.6 kg. or more of active materials per liter can be readily prepared.

Generally the water containing herbicidal composition concentrates of this invention will contain from about 5 to 60 parts by weight active ingredient, from 0.5 to 10 parts by weight of a surface active agent and from 50 to 95 parts by weight of water, the total parts by weight of all constituents being 100. These concentrates are usually diluted further with water to provide sprayable compositions containing from 0.2 to 0.5 kilograms per each 80 to 320 liter of solution in order that sufficient sprayable composition be available to adequately cover the area contemplated to be sprayed with the proper concentration of active ingredient.

The phytotoxicant compositions of this invention preferably contain as a conditioning agent one or more surface-active agents in amounts sufficient to render a given composition readily dispersible in water. The incorporation of a surface-active agent into the compositions greatly enhances their efficacy. By the term "surface-active agent" it is understood that wetting agents, dispersing agents, suspending agents and emulsifying agents are included therein. Anionic, cationic and non-ionic agents can be used with equal facility.

Preferred wetting agents are alkyl benzene and alkyl naphthalene sulfonates, sulfated fatty alcohols, amines or acid amides, long chain acid esters of sodium isotheonate, esters of sodium sulfosuccinate, sulfated or sulfonated fatty acid esters petroleum sulfonates, sulfonated vegetable oils, acetylenic glycols, polyoxyethylene derivatives of alkylphenols (particularly isooctylphenol and nonylphenol) and polyoxyethylene derivatives of the mono-higher fatty acid esters of hexitol anhydrides (e.g. sorbitan). Preferred dispersants are methyl cellulose, polyvinyl alcohol, sodium lignin sulfonates, polymeric alkyl naphthalene sulfonates, sodium naphthalene sulfonate, polymethylene bisnaphthalenesulfonate, sodium N-methyl-N-(long chain acid) taurates and α-alkyl ($C_{12}C_{18}$) omega-hydroxy poly(oxyethylene), the polyoxyethylene content averaging 3 to 20 moles; α(p-alkyl phenyl) omega hydroxy poly(oxyethylene) produced by the condensation of 1 mole of alkyl phenol with 6 moles of ethylene oxide; alkyl ($C_8$–$C_{18}$) sulfate, ammonium, calcium, magnesium, potassium, sodium and zinc salts; α-hydro-omega hydroxy poly(oxyethylene) molecular weight 200–9,500; α-(p-nonyl phenyl) omega-hydroxy poly(oxyethylene) produced by the condensation of 1 mole of nonyl phenol with an average of from 4–14 or 30–90 moles of ethylene oxide; α(p-nonyl phenyl) omega-hydroxy poly (oxyethylene), 4–14 mole average polyoxyethylenes, mixture of dihydrogen phosphate or monohydrogen phosphate esters and the corresponding ammonium, calcium, magnesium, monoethanol amine, potassium, sodium, and zinc salts of the phosphate esters; and amine salts of alkyl ($C_8$–$C_{24}$) benzenesulfonic acid, butyl amine, dimethylaminopropylamine, mono and diisopropylamine, mono, di, and triethanol amine.

Water-dispersible powder compositions can be made containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The water-dispersible powder of this invention usually contains from about 5 to about 95 parts by weight of active ingredient, from about 0.25 to 25 parts by weight of wetting agent, from about 0.25 to 25 parts by weight of dispersant and from 4.5 to about 94.5 parts by weight of inert solid extender, all parts being by weight of the total composition. Where required, from about 0.1 to 2.0 parts by weight of the solid inert extender can be replaced by a corrosion inhibitor or anti-foaming agent or both.

Although compositions of this invention can also contain other additaments, for example fertilizers, phytotoxicants and plant growth regulants, pesticides and the like used as adjuvants or in combination with any of the above-described adjuvants, it is preferred to employ the compositions of this invention alone with sequential treatments with the other phytotoxicants, fertilizers and the like for maximum effect. For example, the field could be sprayed with a composition of this invention either before or after being treated with fertilizers, other phytotoxicants and the like. The compositions of this invention can also be admixed with the other materials, e.g. fertilizers, other phytotoxicants, etc., and applied in a single application. Chemicals useful in combination with the active ingredients of this invention either simultaneously or sequentially include for example triazines, ureas, carbamates, acetamides, acetanilides, uracils, acetic acids, phenols, thiolcarbamates, triazoles, benzoic acids, nitriles and the like such as:

3-amino-2,5-dichlorobenzoic acid
3-amino-1,2,4-triazole
2-methoxy-4-ethylamino-6-isopropylamino-s-triazine
2-chloro-4-ethylamino-6-isopropylamino-s-triazine
2-chloro-N,N-diallylacetamide
2-chloroallyl diethyldithiocarbamate
N'-(4-chlorophenoxy) phenyl-N,N-dimethylurea
1,1'-dimethyl-4,4'-bipyridinium dichloride
isopropyl n-(3-chlorophenyl) carbamate
2,2-dichloropropionic acid
S-2,3-dichloroallyl N,N-diisopropylthiolcarbamate
2-methoxy-3,6-dichlorobenzoic acid
2,6-dichlorobenzonitrile
N,N-dimethyl-2,2-diphenylacetamide
6,7-dihydrodipyrido (1,2-a:2',1'-c)-pyrazidiinium salt
3-(3,4-dichlorophenyl)-1,1-dimethylurea
4,6-dinitro-o-sec-butylphenol
2-methyl-4,6-dinitrophenol
ethyl N,N-dipropylthiolcarbamate
2,3,6-trichlorophenylacetic acid
5-bromo-3-isopropyl-6-methyluracil
3-(3,4-dichlorophenyl)-1-methoxy-1-methylurea
2-methyl-4-chlorophenoxyacetic acid
3-(p-chlorophenyl)-1,1-dimethylurea
1-butyl-3-(3,4-dichlorophenyl)-1-methylurea
N-1-naphthylphthalamic acid
1,1'-dimethyl-4,4'-bipyridinium salt
2-chloro-4,6-bis(isopropylamino)-s-triazine
2,4-dichlorophenyl-4-nitrophenyl ether
alpha, alpha, alpha-trifluoro-2,6-dinitro-N,N-dipropyl-p-toluidine
S-propyl dipropylthiolcarbamate
2,4-dichlorophenoxyacetic acid
N-isopropyl-2-chloroacetanilide
2',6'-diethyl-N-methoxymethyl-2-chloroacetanilide
2-chloro-4,6-bis(ethylamino)-s-triazine
monosodium acid methanearsonate
disodium methanecarsonate N-(1,1-dimethylpropynyl)-3,5-dichlorobenzamide and giberrellin Fertilizers useful in combination with the active ingredients include for example ammonium nitrate, urea, potash, and superphosphate.

When operating in accordance with the present invention, effective amounts of the glycines are applied to above ground portions of plants. The application of liquid herbicidal compositions to above ground portions of plants can be carried out by conventional methods, e.g. power dusters, boom and hand sprayers and spray dusters. The compositions can also be applied from airplanes as a spray because of their effectiveness at low dosages. The application of herbicidal compositions to aquatic plants is usually carried out by spraying the compositions on the aquatic plants in the area where control of the aquatic plants is desired.

The application of an effective amount of the compounds of this invention to the plant is essential and critical for the practice of the present invention. The exact amount of active ingredient to be employed is dependent upon the response desired in the plant as well as such other factors as the plant species and stage of development thereof, and the amount of rainfall as well as the specific glycine employed. In foliar treatment for the control of vegetative growth, the active ingredients are applied in amounts from about 0.0112 to about 25 or more kilograms per hectare. In applications for the control of aquatic plants, the active ingredients are applied in amounts of from about 0.01 parts per million to about 1000 parts per million, based on the aquatic medium. An effective amount for phytotoxic or herbicidal control is that amount necessary for overall or selective control, i.e. a phytotoxic or herbicidal amount. It is believed that one skilled in the art can readily determine from the teachings of this specification, including examples, the approximate application rate.

Although this invention is described with respect to specific modifications, the details thereof ae not to be construed as limitations except to the extent indicated in the following claims.

What is claimed is:

1. A compound of the formula

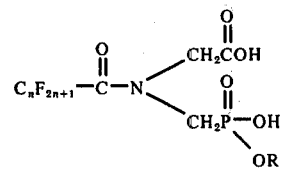

wherein R is a member of the group consisting of H and

and $n$ is an integer of from 1 to 4.

2. A compound of claim 1 wherein R is a

grouping wherein $n$ is from 1 to 4.

3. A compound of claim 2 which is bis(N,O-trifluoroacetyl)-N-phosphonomethyl glycine.

4. A compound of claim 2 which is bis-(N,O-heptafluorobutyryl)-N-phosphonomethyl glycine.

5. A herbicidal composition comprising a herbicidally acceptable surfactant, an inert diluent and a herbicidally effective amount of a compound of claim 1.

6. A herbicidal composition comprising a herbicidally acceptable surfactant, an inert diluent and a herbicidally effective amount of a compound of claim 2.

7. A herbicidal composition comprising a herbicidally acceptable surfactant, an inert diluent and a herbicidally effective amount of a compound of claim 3.

8. A herbicidal composition comprising a herbicidally acceptable surfactant, an inert diluent and a herbicidally effective amount of a compound of claim 4.

9. A method of controlling undesirable plants which comprises contacting said plants with a herbicidal amount of a compound of claim 1.

10. A method of controlling undesirable plants which comprises contacting said plants with a herbicidal amount of a compound of claim 2.

11. A method of controlling undesirable plants which comprises contacting said plants with a herbicidal amount of a compound of claim 3.

12. A method of controlling undesirable plants which comprises contacting said plants with a herbicidal amount of a compound of claim 4.

* * * * *